(12) United States Patent
Parker et al.

(10) Patent No.: US 10,952,766 B2
(45) Date of Patent: Mar. 23, 2021

(54) CIRCUMCISION DEVICE (71) Applicant: INNOVATIVE MEDICAL TECHNOLOGY(PTY) LTD, Cape Town (ZA)

(72) Inventors: Cyril Norman Parker, Cape Town (ZA); Elisabeth Regina Parker, Cape Town (ZA); Jared Mark Vorster, Cape Town (ZA); David Christopher Wiseman, Cape Town (ZA)

(73) Assignee: INNOVATIVE MEDICAL TECHNOLOGY (PTY) LTD, Cape Town (ZA)

( * ) Notice: Subject to any disclaimer, the term of this patent is extended or adjusted under 35 U.S.C. 154(b) by 0 days.

(21) Appl. No.: 16/477,101

(22) PCT Filed: Jan. 12, 2018

(86) PCT No.: PCT/IB2018/050204
§ 371 (c)(1),
(2) Date: Jul. 10, 2019

(87) PCT Pub. No.: WO2018/130983
PCT Pub. Date: Jul. 19, 2018

(65) Prior Publication Data
US 2019/0350611 A1    Nov. 21, 2019

(30) Foreign Application Priority Data
Jan. 13, 2017 (ZA) .................. 2017/00296

(51) Int. Cl.
*A61B 17/326* (2006.01)
*A61B 17/00* (2006.01)
*A61B 17/32* (2006.01)

(52) U.S. Cl.
CPC .... *A61B 17/326* (2013.01); *A61B 2017/0023* (2013.01); *A61B 2017/00477* (2013.01); *A61B 2017/320052* (2013.01)

(58) Field of Classification Search
CPC ............ A61B 17/326; A61B 17/12009; A61B 17/1322; A61B 2017/0023;
(Continued)

(56) References Cited

U.S. PATENT DOCUMENTS 5,797,921 A  *  8/1998  Cimini ................. A61B 17/326
                                                                606/118
2007/0060928 A1*  3/2007  Dave .................... A61B 17/326
                                                                606/118
(Continued)

FOREIGN PATENT DOCUMENTS

EP      2345379 A1    7/2011
WO    2009/114529 A2    9/2009
(Continued)

OTHER PUBLICATIONS

International Search Report and Written Opinion for PCT/IB2018/050204, dated Apr. 13, 2018.

*Primary Examiner* — Mohamed G Gabr
(74) *Attorney, Agent, or Firm* — Merchant & Gould P.C.

(57) ABSTRACT

A circumcision device is provided by the present invention and includes a body and a glans penis locating and protecting member permanently or releasably associated with the body. The body and glans penis locating member between them support a foreskin crushing assembly that includes a crushing surface that includes an axis extending in the general direction of a penis being circumcised in use, a cooperating crushing member, and a mechanism for operating the foreskin crushing assembly. A cutting assembly is also provided that is rotatable about said axis relative to the crushing surface so as to be capable of severing a foreskin (Continued)

adjacent the foreskin crushing assembly. The cutting assembly includes a cutting blade movable between a withdrawn position and an operative extended condition in which the blade may be rotated about said axis to cooperate with the crushing surface or a foreskin located thereon.

14 Claims, 5 Drawing Sheets

(58) Field of Classification Search
CPC .. A61B 2017/0073; A61B 2017/12018; A61H 19/32
See application file for complete search history.

(56) References Cited

U.S. PATENT DOCUMENTS

| | | | | |
|---|---|---|---|---|
| 2012/0303041 | A1* | 11/2012 | Marczyk | A61B 17/326 |
| | | | | 606/118 |
| 2013/0325026 | A1* | 12/2013 | Fuerst | A61B 17/326 |
| | | | | 606/118 |

FOREIGN PATENT DOCUMENTS

| | | | | |
|---|---|---|---|---|
| WO | 2014/094005 | A1 | 6/2014 | |
| WO | 2015/155724 | A1 | 10/2015 | |
| WO | WO-2015155724 | A1 * | 10/2015 | ........... A61B 17/326 |

* cited by examiner

CIRCUMCISION DEVICE

CROSS-REFERENCE TO RELATED APPLICATIONS

This application is a National Stage Application of PCT/IB2018/050204, filed 12 Jan. 2018, which claims benefit of priority to South African provisional patent application number 2017/00296 filed on 13 Jan. 2017, which are incorporated herein by reference. To the extent appropriate, a claim of priority is made to each of the above-disclosed applications.

FIELD OF THE INVENTION

This invention relates to a circumcision device for conducting circumcision of a male person, especially, but not necessarily, an adolescent, a teenager or an adult male. More particularly the circumcision device of the invention is preferably made as a single use device to avoid the transfer of infection from one person to another. The device is preferably designed to be assembled from a limited number of components and to avoid misuse thereof.

BACKGROUND TO THE INVENTION

Circumcision of male persons is carried out for any one of a number of different reasons including religious and health reasons.

Human immunodeficiency virus (HIV) is a blood-borne virus that affects millions of people each year. The majority of worldwide infections have occurred in sub-Saharan Africa, where 19.2 million individuals were reported HIV-positive in 2014.

Male circumcision has been shown to decrease a man's chances of contracting HIV from an HIV positive female partner by of the order of 60%. Based on this, circumcision as a method of combating the contracting of HIV has the potential to avert many new infections each year. This drastic reduction has prompted a push to circumcise approximately 30 million adult males by 2021 in an environment in which less than 30% of males in Africa are circumcised.

One of the 2020 strategic targets of UNAIDS is that 27 million men in high prevalence settings are voluntarily medically circumcised, as part of an integrated services for men.

The circumcision process has remained largely unaltered for the past few decades. Commonly, a Gomco clamp that has been in use since 1935 is used as a surgical assist instrument. Alternatively, a freehand incision (classical) may be used usually by a surgeon to perform a circumcision that is followed by the introduction of sutures. Both of these require the use of a scalpel with a handle to complete the circumcision.

The Gomco clamp works by exerting a crushing force on the foreskin in a crush zone created in a gap between the divergent outer crushing surface of a glans penis location member (termed a bell in the instance of the Gomco clamp) and a periphery of a crush aperture in a crush plate so that the skin can be cut away after a period of time. This clamping creates a "hemostatic seal" along the cut edge, which obviates the need for sutures. Whilst the Gomco device provides a simple, safe method for circumcision it is not necessarily ideal for the large numbers of circumcision procedures targeted in Sub-Saharan Africa.

In the first place, the Gomco Clamp and other surgical assist circumcision devices such as the Unicirc, Simplecirc and Mogenclamp require the use of a scalpel to cut the foreskin adjacent the crush zone. Due to the massive number of circumcisions clinicians or doctors need to be able to perform and many of whom could be HIV positive patients, there is a concern about the exposure of personnel and patients to any sharp devices.

Secondly, many circumcision devices including the Gomco clamp are re-usable devices and the WHO (World Health Organization) recommends that the ideal circumcision device should have as few parts as possible once assembled for use and requires that a circumcision device has to be restricted to a single use only in that it has to actively resist attempts to be reused.

Non-surgical assist circumcision devices that typically include rings and clamps (like the Prepex, Shangring, Tara KLamp, Ismail clamp, Plastibell, Alisclamp) also need to be single use devices. Plastic devices generally need to be left on the body for 5 to 7 days after which time they have to be removed. A device that is left in place for an extended period of time is preferably not used due to excessive complications with scheduling follow up visits for the removal of the device. Additionally, there is a concern that the popularity of the entire circumcision program could be affected by a foul smell that may accompany wearing the device as the skin begins to die and decompose which also increases the risk of infection with bacteria such as tetanus.

There are currently no commercially available devices of which applicant is aware that both eliminate exposure to separate sharp objects and are single-use devices.

As regards published material describing attempts to fulfill the requirements of a single use circumcision device, international publication number WO2014094005 describes a circumcision device having a central glans penis locating member having a divergent outer crushing surface cooperating with the periphery of a crush aperture in a crush plate. The locating member and crush plate are axially movable relative to each other so that a gap between the crushing surface and crush aperture can be varied to effect crushing of foreskin that is positioned between them in well-known manner. The means for effecting axial movement in this case is a pair of diametrically opposite screw threaded members located on opposite sides of the central glans penis locating member. In this instance single use is achieved by making the diametrically opposite screw threaded members that control the gap in the crush zone between the crushing surface and crush aperture such that they cannot be released sufficiently to introduce a subsequent foreskin after a first foreskin has been removed from the crush area.

A similar arrangement is described in international publication number WO2015155724 in which relative axial movement is achieved using a single screw threaded wing nut cooperating with a central tubular body having a glans penis locating end and an opposite operating end at which the wing nut is located. In this instance single use is achieved by making the central tubular body such that it cannot be released sufficiently to introduce a subsequent foreskin after a first one has been removed from the crush area. In each case it is possible to dislocate or release the glans penis locating member. This may be considered to be a disadvantage in resulting in too many loose or separate components for disposal after completion of a procedure which encourages manipulation and possible attempts at re-use of components. Also multiple components may be a challenge as compared to disposal of one assembled unit instrument.

Nevertheless, neither of these addresses the possible dangers of using separate scalpels or the like whilst their construction actually necessitates that a scalpel or the like is used to sever the crushed foreskin.

In order to provide for the number of circumcisions necessary to impede the spread of HIV, a safe, reliable, and quick circumcision device and method are required that do not require the use of a separate scalpel or the like.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with this invention there is provided a circumcision device comprising a body and a glans penis locating and protecting member permanently or releasably associated with the body and wherein the body and glans penis locating member between them support a foreskin crushing assembly that includes an endless crushing surface over which a foreskin to be circumcised is locatable in use wherein the crushing surface has an axis extending in the general direction of a penis being circumcised in use, a cooperating crushing member, and a mechanism for operating the foreskin crushing assembly, the circumcision device being characterized in that it includes a cutting assembly rotatable about said axis relative to the crushing surface so as to be capable of severing a foreskin adjacent the foreskin crushing assembly and wherein the rotatable cutting assembly includes a cutting blade movable between a first withdrawn position relative to the crushing surface and operative extended conditions in which the blade may be rotated about said axis to cooperate with the crushing surface or a foreskin located thereon adjacent the crushing assembly so as, in use, to sever a foreskin located over the crushing surface.

Further features of the invention provide for the rotatable cutting assembly to be of generally ring shape; for the rotatable cutting assembly to include a blade carried by, or forming part of, a pivotally retractable blade arm that is attached to the rotatable cutting assembly at a mounted end of the blade arm by means of an articulated attachment such as a pivot so as to be movable between at least a first withdrawn inoperative position and extended operative positions in which the blade is located inwards of the articulated attachment and either trailing or leading the retractable arm; for the rotatable cutting assembly to be manually rotatable relative to the body; for the rotatable cutting assembly to be configured such that a force applied to the rotatable cutting assembly urges the blade toward the crushing surface so as to cut any foreskin located on the crushing surface; for the cutting assembly to be configured such that a plurality of revolutions of the assembly are required to sever a foreskin located on the crushing surface; and for the blade to have a second withdrawn inoperative position that may be reached by causing movement of the blade from an operative position past its first withdrawn inoperative position into said second withdrawn inoperative position in which it resists subsequent deployment to any operative position to thereby provide an optional expedient for rendering the circumcision device a single use circumcision device.

Still further features of the invention provide for the rotatable cutting assembly to include two relatively rotatable components in the form of a base ring that is preferably rotatable immediately adjacent a crushing plate carried by the body and a swivel ring that is rotatable to a limited extent relative to the base ring and that is preferably held non-rotatable relative to the body by a removable tab or a frangible connection; for one of the base ring and swivel ring to have a pivot supporting a mounted end of a blade carried by, or forming part of, a pivotally retractable blade arm; for the other of the base ring and swivel ring to have one or more formations for engaging the blade carrying arm to urge it inwards towards the crushing surface by transferring at least some of any rotational force applied to the ring assembly; and for the swivel ring to have a plurality of equally angularly spaced finger stops that are preferably angularly spaced about the swivel ring and arranged to facilitate rotation in a direction corresponding to operative engagement of the blade with a foreskin or crushing surface.

Preferably the body is a separate component from the glans penis locating member and a series of differently sized glans penis locating members having like portions for common co-operation with the body and co-operating crushing plates is provided so that an appropriate size of glans penis locating member and co-operating crushing plate can be selected for use in conjunction with the body in respect of a particular patient.

Additional features of the invention provide for the foreskin crushing assembly to include an endless crushing surface formed as or in a periphery of an aperture through a crushing plate attached such as by clipping to the body and with which a selected divergent outer crushing surface on the outside of the glans penis locating member co-operates; for the body to be an optionally reinforced injection moulded plastics body to which the crushing plate is fixed wherein the body has a collar co-axial with, but spaced apart from, the aperture in the crushing plate with the collar preferably being integral with the body; for the glans penis locating member to be tubular and to have on the outside thereof projections co-operating with catches in a bore of the collar to prevent removal of the glans penis locating member from the body once a single use has been performed and thereby to contribute towards or render the device a single use device; for the collar to co-operate with a relatively screw threaded, manually rotatable nut configured to co-operate with an externally screw threaded zone of a glans penis locating member to function as the mechanism for operating the foreskin crushing assembly to axially move the crushing surface relative to the crushing plate so that a gap between the crushing surface and aperture can be closed to effect crushing of foreskin that is positioned between them in well-known manner; and for the glans penis locating member to have at least one formation for restricting its movement to axial movement without any rotation thereof.

It will be understood that the body and rotatable cutting assembly on the one hand and the crushing plate and co-operating size of glans penis locating member on the other hand, will be made available as separate components for selective association according to a patient to be treated.

In order that the above and other features of the invention may be more fully understood, one embodiment of the invention will now be described, by way of example only, with reference to the accompanying drawings.

DETAILED DESCRIPTION WITH REFERENCE TO THE DRAWINGS

In the embodiment of the invention illustrated in the drawings, a circumcision device comprises a body (1) and a glans penis locating member (2) for association with the body (1) by way of a relatively rotatable double wing nut (3) held captive relative to a collar (4) that is integral with the body (1) at an operating end thereof. The wing nut (3) receives, in use, a screw threaded end (5) of the glans penis locating member (2) that extends generally axially relative to the wing nut (3) and away from the operating end of the body (1) towards a foreskin crushing assembly that is more fully described below.

The glans penis locating member (2) is generally tubular and has an opposite end region having an outer surface forming a part of the foreskin crushing assembly that includes an endless crushing surface in the form of a divergent generally truncated conical outer crushing surface (6) on the glans penis locating member (2). That crushing surface (6) co-operates in use with a suitably profiled periphery of an aperture (7) through a crushing plate (8) attached, in this instance, by clipping it to the body (1) using two diametrically opposite integral clips (9). Additional holes and projections (10) may serve to more accurately locate the crushing plate (8) on a support frame (11) located at a crushing end of the circumcision device. The crushing surface (6) and the aperture (7) through the crushing plate (8) together form the crushing assembly.

The body (1) may be made of an optionally reinforced injection or dough moulded plastics material and is of generally arch shape with the collar (4) at the central operating end thereof and spaced apart from the collar (4), the integral generally oval support frame (11) that is orientated in a plane that is transverse and in this instance at generally right angles to the axis of the glans penis locating member (2) at a foreskin crushing end thereof at which the crushing plate (8) is clipped to the support frame.

The tubular glans penis locating member (2) has on the outside thereof circumferential projections (12) co-operating with catches (13) in a bore of the collar (4) to prevent removal of the glans penis locating member (2) from the body (1) once a single use has been performed. This feature thereby contributes towards, or renders, the circumcision device a single use device.

Figure 1:
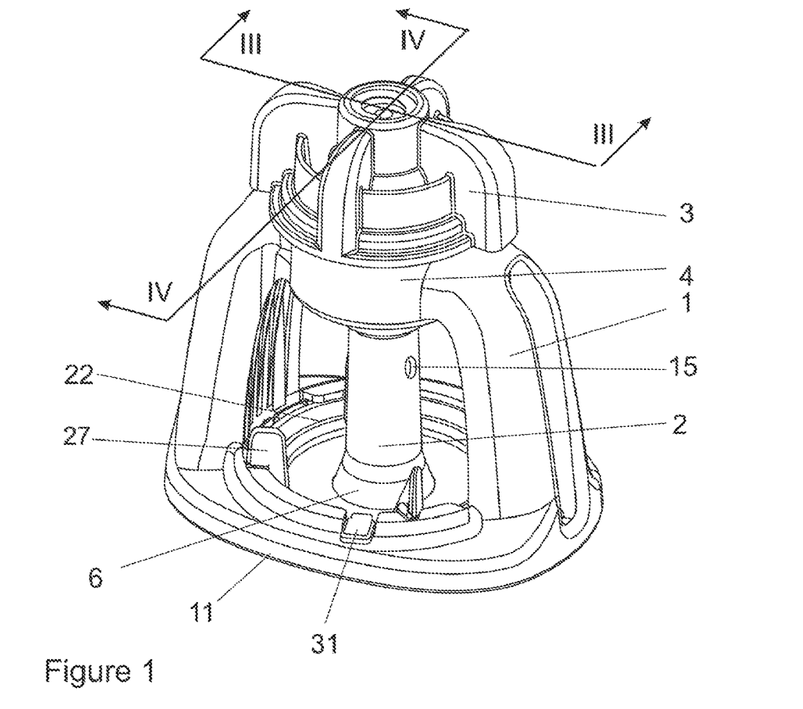
FIG. 1 is a three dimensional view of one embodiment of a circumcision device according to the invention showing an operating end thereof having a double wing nut for operating the crushing assembly.
Figure 2:
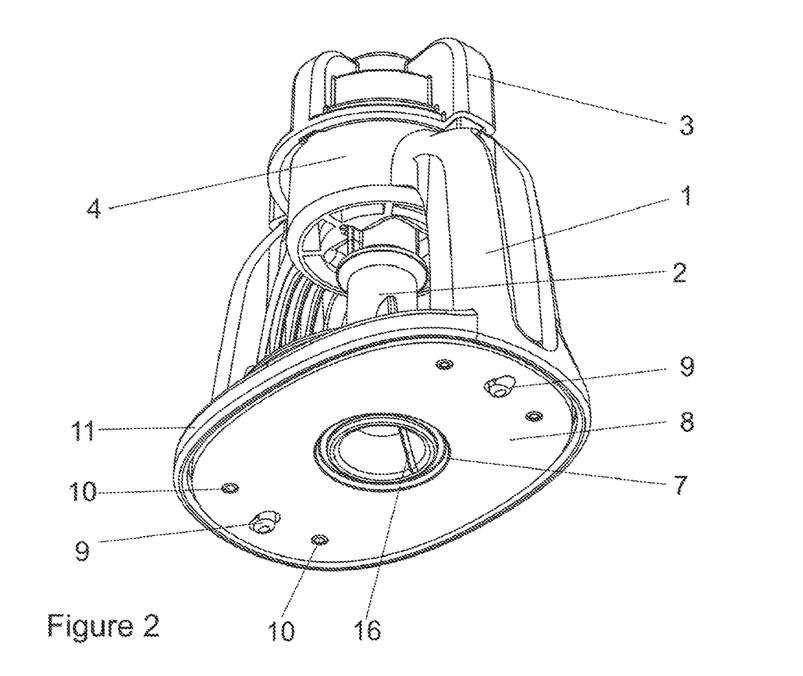
FIG. 2 is a three dimensional view of the circumcision device showing an opposite end thereof and showing the crushing assembly in a substantially closed condition.
Figure 3:
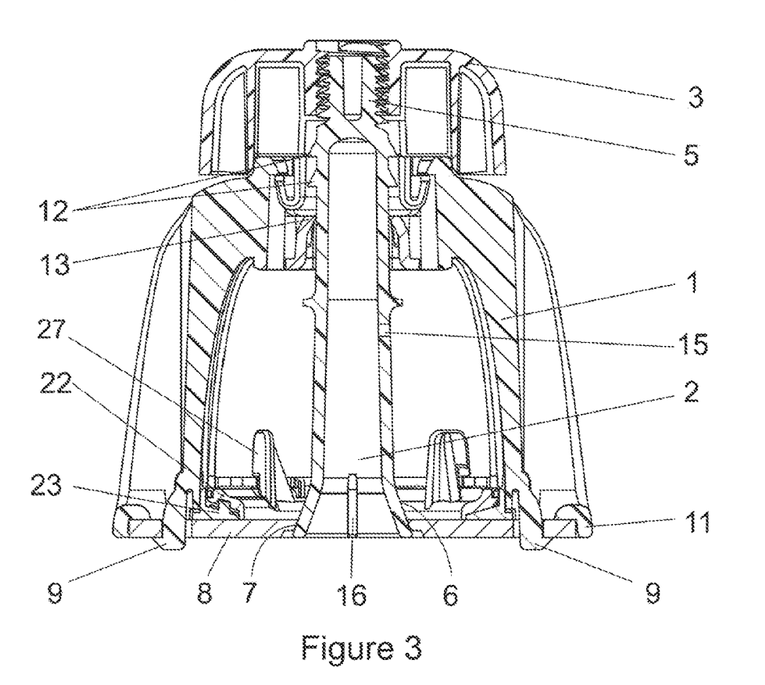
FIG. 3 is a sectional elevation taken along line III to HI in FIG. 1.
Figure 4:
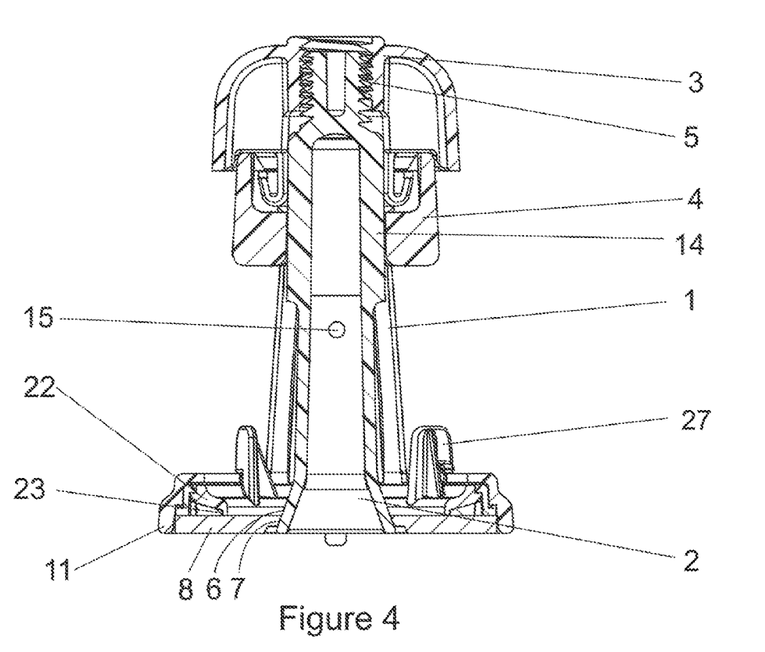
FIG. 4 is a sectional side view taken along line W to IV in FIG. 1.
Figure 5:
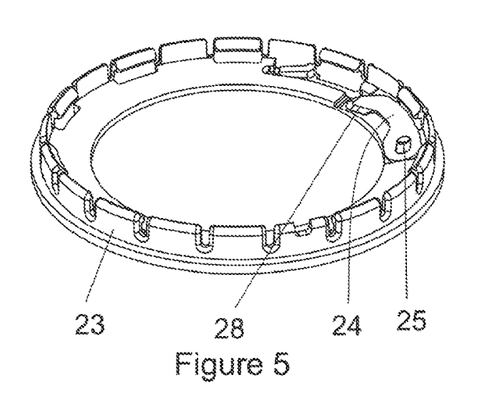
FIG. 5 is a three dimensional view of a base ring of a rotatable cutting assembly with the blade arm in a retracted position.

Also, the outer surface of a part the length of the glans penis locating member (2) associated with the operating end has a longitudinally extending ridge (14) (see especially FIG. 8) that co-operates with a groove in the collar (4) (as is apparent from FIG. 4) to hold the glans penis locating member (2) non-rotatable relative to the body (1) to ensure axial crushing of a foreskin in use in well-known manner.

The collar (4) thus co-operates with the screw threaded, manually rotatable double wing nut (3) by way of the externally screw threaded zone of the glans penis locating member (2) to function as a mechanism for operating the foreskin crushing assembly by axially moving the crushing surface (6) relative to the crushing plate (8) so that a gap between the crushing surface (6) and aperture (7) in the crushing plate (8) can be narrowed to effect crushing of foreskin that is positioned between them.

The collar (4) and double wing nut (3) may result in the tubular glans penis locating member (2) being closed at its operating end and it may be advantageous to provide one or more holes (15) through the wall of the tubular glans penis locating member (2) in order to ensure that the internal pressure can be at atmospheric pressure. Also, the inside surface of the truncated conical part of the tubular glans penis locating member (2) may be provided with one or more longitudinally extending grooves (16) that can be used to align with the frenulum at installation on a penis should that be relevant for any particular reason.

Consequent on the different sizes of penis that may require circumcision, and whilst the screw threaded end (5) region section of the glans penis locating member (2) may be the same to ensure proper co-operation with the nut (3), a range of glans penis locating members may be provided with different sizes of the tubular glans penis locating member sections and associated generally truncated conical outer crushing surface (6) may be provided so that a selection can be made for each patient. Sizes may, for example be in the range of 20 mm to 36 mm or any other appropriate range depending on the general type of patient being targeted. The two different axial sections of the glans penis locating member (2) are indicated by the letters "a" and "b" in FIG. 8.

Figure 8:
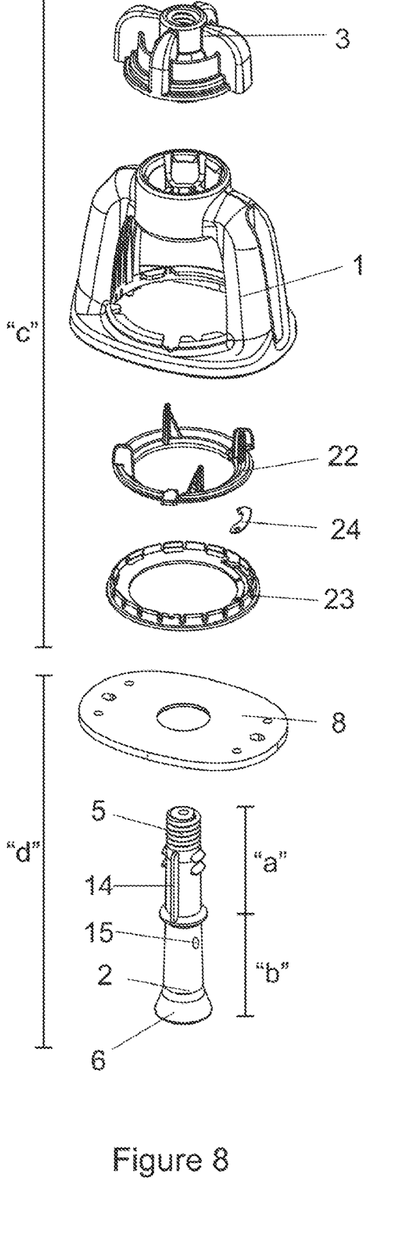
FIG. 8 is an exploded three dimensional view of the circumcision device illustrating the groupings of the various components.

Accordingly, the body (1) and cutting assembly indicated by the letter "c" in FIG. 8, is generally made as a separate component from the glans penis locating member (2) and crushing plate (8) indicated by the letter "d" in FIG. 8. This enables a series of differently sized glans penis locating members and co-operating crushing plates to be provided so that an appropriate size of glans penis locating member and co-operating crushing plate can be selected for use in conjunction with a standard body assembly in respect of a particular patient.

Figure 9:
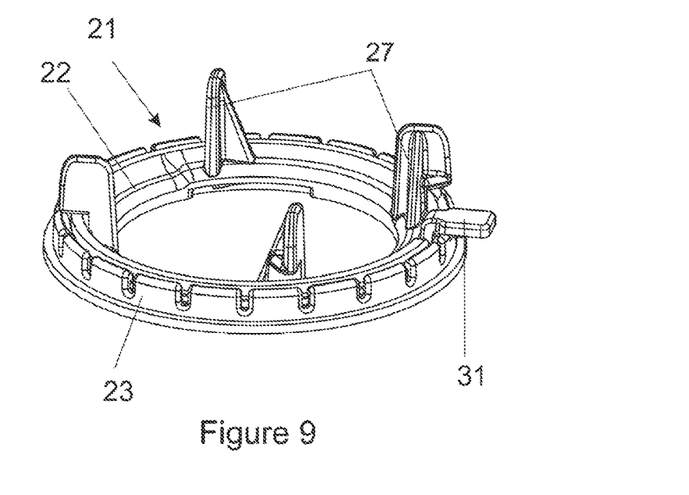
FIG. 9 is a three dimensional view of the ring shaped rotatable cutting assembly.

As provided by this invention, the circumcision device includes a generally ring shaped cutting assembly (21) (see especially FIG. 9) rotatable about the axis relative to the crushing surface (6) of the glans penis locating member (2) so as to be capable of severing a foreskin adjacent the foreskin crushing assembly. The rotatable cutting assembly (21) is composed of two rings being a swivel ring (22) and a base ring (23) that supports an end of a blade arm (24) by way of a pivot (25) carried by the base ring (23) with the blade arm being confined to movement in a plane at right angles to the axis of the circumcision device. The swivel ring (22) has four equally angularly spaced finger stops (27) arranged to facilitate manual rotation of the swivel ring (22) in a direction corresponding to operative engagement of the blade with a foreskin positioned over the crushing surface (6).

The blade arm is thus movable between a first radially withdrawn position relative to the crushing surface (6) and operative extended conditions in which a blade (28) at the other end of the blade arm may be rotated about the axis to cooperate with the crushing surface (6) or a foreskin located thereon immediately adjacent the crushing assembly to sever a foreskin located on the crushing surface (6). The base ring (23) is held rotatable but captive relative to a circular co-axial aperture in the generally oval support frame (11) and the swivel ring (22) is held rotatable but captive relative to the base ring (23) so as to be relatively rotatable to a limited extent as will become more apparent from what follows.

The entire ring shaped cutting assembly (21) is held temporarily non-rotatable relative to the generally oval support frame by a radially extending removable tab (31) that engages in a recess in the periphery of the surrounding frame and that can be disengaged from the recess such as by tearing it off to render the ring shaped cutting assembly (21) rotatable once a clinician is satisfied that crushing has been properly effected and any time required for blood flow cessation has expired. Other frangible connections may be employed for this purpose.

Figure 6:
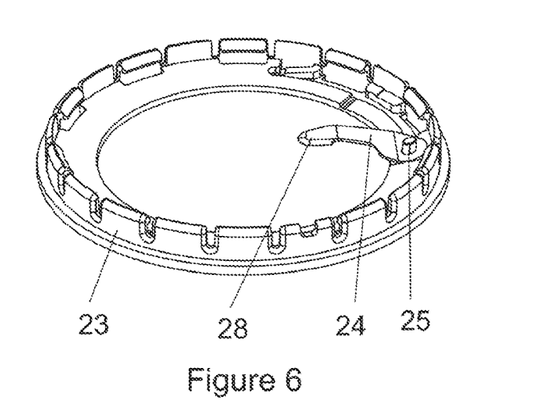
FIG. 6 is the same as FIG. 5 but showing the cutting arm in an operative position.
Figure 7:
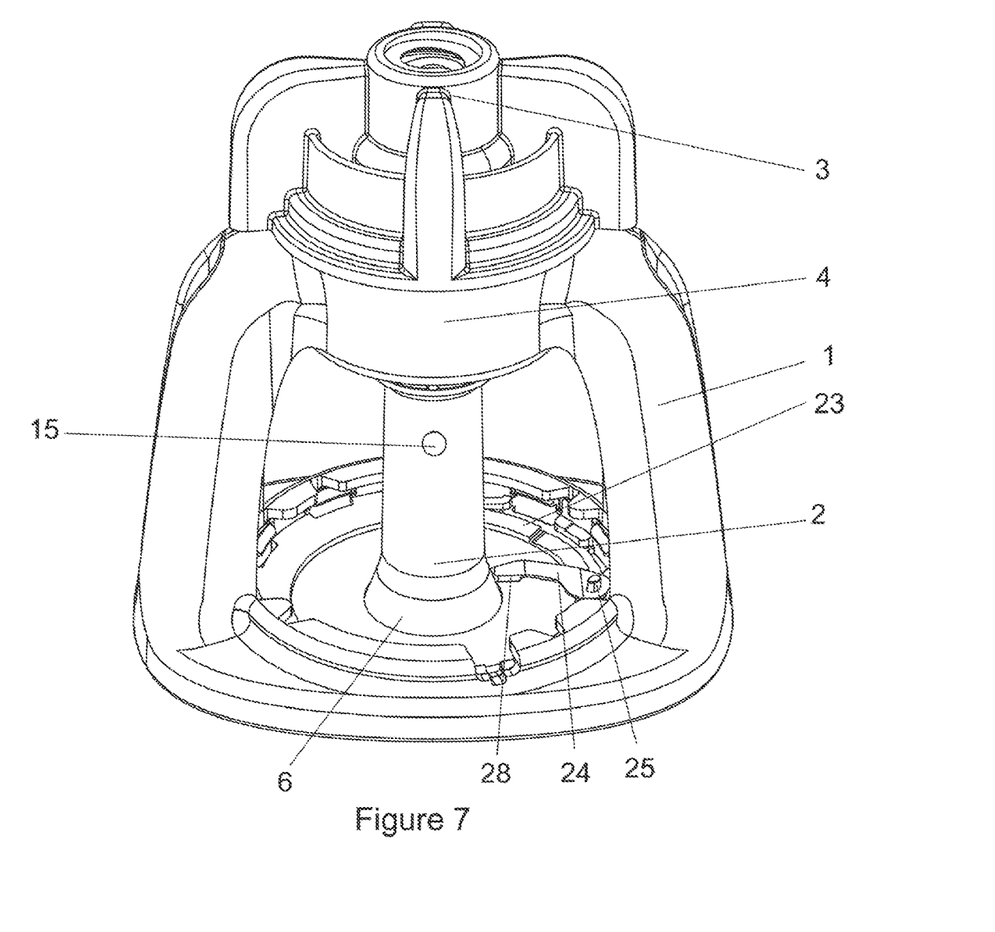
FIG. 7 is a three dimensional view of the circumcision device with the swivel ring removed and the blade arm in an operative position.
Figure 10:
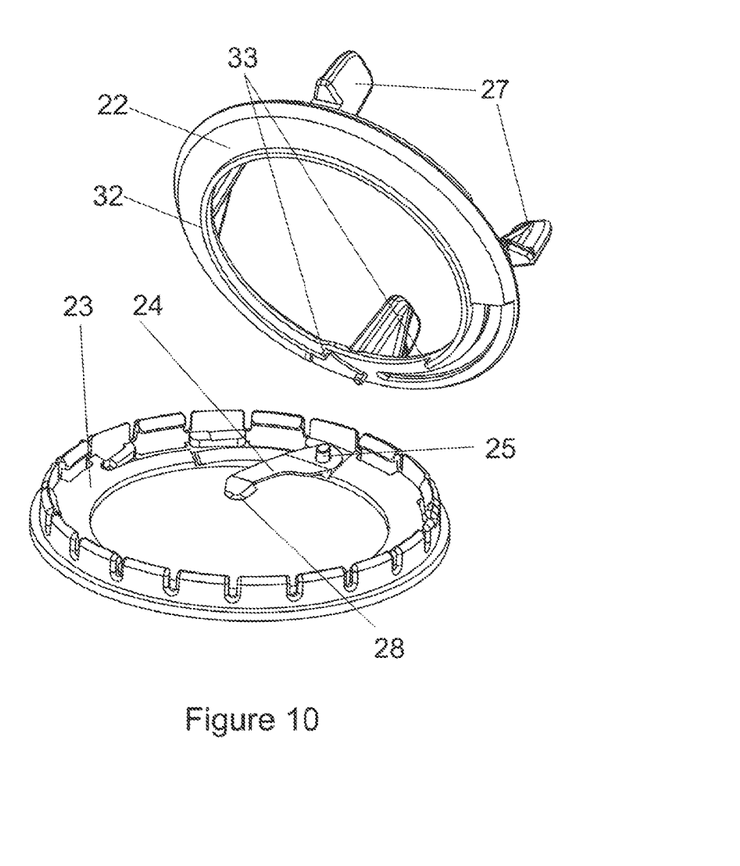
FIG. 10 is a three dimensional view of the ring shaped rotatable cutting assembly showing the swivel ring in exploded and somewhat tipped rearwards to show the co-operating faces thereof.
Figure 11:
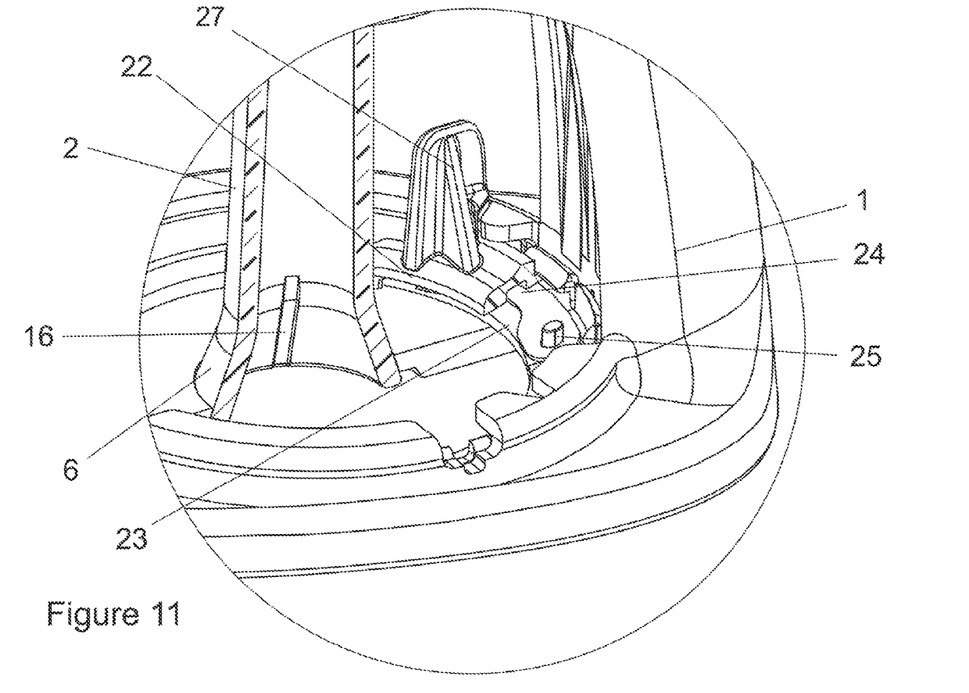
FIG. 11 is a partly cut away detail of part of the circumcision device showing the blade arm in a retracted position and partially covered by a portion of the swivel ring; and, FIG. 12 is the same as FIG. 11 but showing the blade arm in a retracted position and visible.
Figure 12:
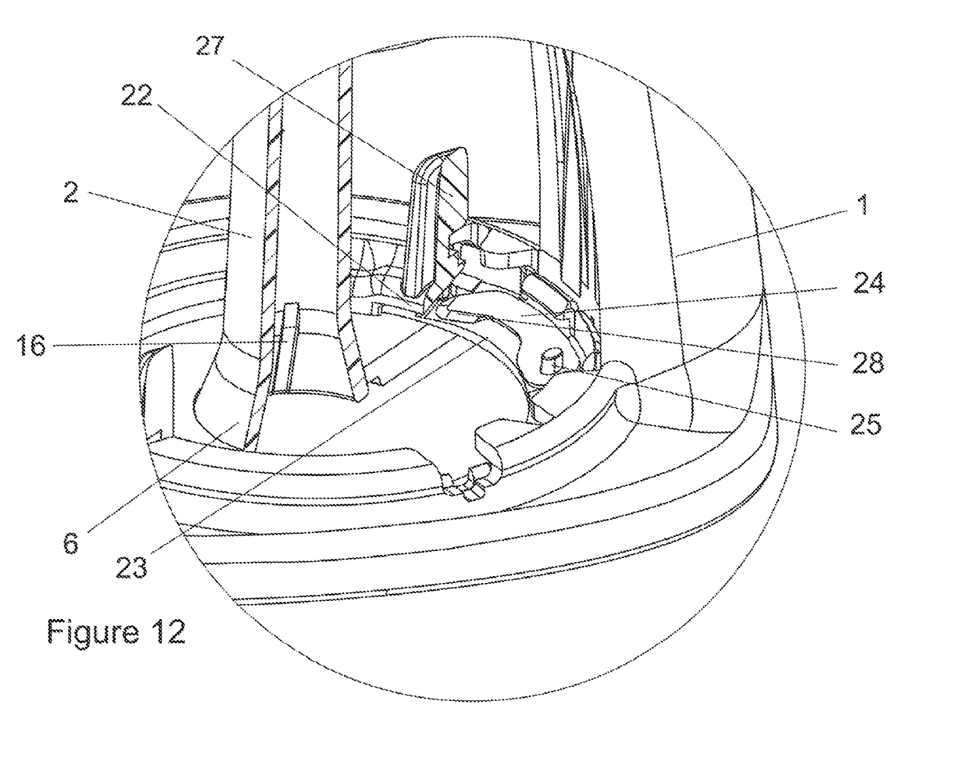

The blade arm is movable between a first withdrawn inoperative position in which it is ready for deployment, as shown in FIGS. 5, 9, 11 and 12, and operative extended positions in which the blade is located inwards of the pivotal attachment, as shown in FIGS. 6, 7, and 10. In this embodiment of the invention, the blade at the free end of the blade arm trails the retractable arm although it is possible to configure an arrangement such that the blade leads the arm. As indicated above the rotatable cutting assembly (21) is manually rotatable relative to the body (1) by means of the finger stops and the rotatable cutting assembly (21) is configured such that a force applied to the rotatable cutting assembly (21) urges the blade toward the crushing surface (6) so as to cut any foreskin located on the crushing surface (6). This is achieved by means of a part-circular ridge (32) on the inner surface of the swivel ring (22) that has ends (33) one of which engages the outer edge of the blade arm when the swivel ring (22) is rotated in one direction (clockwise for example) to urge the blade toward the crushing surface (6) and the other of which engages the inner edge of the blade arm when the swivel arm is rotated in the opposite direction (anti-clockwise for example) to urge the blade away from the crushing surface (6) (see FIG. 10). The cutting assembly (21) is configured such that a plurality of revolutions of the cutting assembly (21), say 2 to 4, is required to sever a foreskin located on the crushing surface (6).

The arrangement is also preferably such that the reverse direction of movement of the swivel ring (22) moves the blade arm away from the crushing surface (6) to a second withdrawn inoperative position that is reached by causing movement of the blade arm past its first withdrawn inoperative position into the second withdrawn inoperative position. In the latter position the blade arm is held against subsequent deployment to any operative positions to thereby provide at least one expedient for rendering the circumcision device a single use circumcision device.

It will be understood that each of the components of the circumcision device described above can be made as an injection moulded plastics item of a suitable plastics material with the relevant plastic material optionally being reinforced such as using glass or other suitable fibres as will be quite apparent to those of ordinary skill in the art. The main exception to this is, of course the blade that will generally be made of suitable surgical steel and the optional exception of the crushing plate that could be made of a metal, if required, depending on design factors.

In use, an appropriate size of glans penis locating member (2) for a particular patient is selected as well as a co-operating crushing plate (8). The glans penis locating member (2) can be installed on the penis to be circumcised by folding the foreskin rearwards; locating the glans penis locating member (2) in position and folding the foreskin over the outer divergent crushing surface (6) of the glans penis locating member. The crushing plate (8) is installed on the body (1) by clipping it into position and the crushing assembly operated to crush the foreskin in a required position to stop blood flow to the foreskin. After a suitable period of time, generally of the order of 4 to 6 minutes, the cutting assembly (21) can be deployed by removing the tab and the swivel ring (22) rotated in a clockwise direction to cause the blade to adopt operative positions and sever the foreskin immediately adjacent the crushing plate (8). Typically two or more revolutions of the cutting assembly (21) will be required.

The swivel ring (22) can then be rotated in the reverse (anti-clockwise) direction to cause the blade to retract as will be apparent from the foregoing and move to its second withdrawn position. The crushing assembly can then be released to the limited extent permitted by the circumferential projections (12) co-operating with catches (13) and the crushed skin can be removed in a manner well known to those of ordinary skill in art using a moistened gauze or equivalent to remove a further narrow ring of crushed skin. The entire device can then be removed and any post circumcision treatment administered. The main part of foreskin removed can be treated as may be required in any instance or simply discarded with the glans penis locating member (2) and the remainder of the device if required.

It will be understood that the glans penis locating member (2) will become locked into the body (1) as will be apparent from the foregoing so that the entire device needs to be disposed of in a suitable way as a unit.

At the same time, the blade becomes withdrawn to the second withdrawn position thereby reinforcing the one use only property of the device.

The device provided by this invention has many features that are considered to be advantageous in that it is a single use device that may be non-necrotizing and does not require a long-duration on the body (1).

The device may eliminate or minimize bleeding through application of constant pressure on a target area for around 5 minutes or possibly less.

The device also eliminates or minimizes the use of separate sharp objects and thereby protects patients and medical staff from risk of accidental wounds with the possibility of infection.

The device may be designed to be inexpensive to manufacture and be available in a scalable manner.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A circumcision device comprising a body having a collar and a glans penis locating and protecting member which includes an inside surface on which in use a glans penis is capable of being located and protected, the glans penis locating and protecting member being permanently or releasably associated with the body, wherein the body and glans penis locating and protecting member support a foreskin crushing assembly that includes a cooperating crushing member and a crushing surface of the glans penis locating and protecting member over which a foreskin to be circumcised is locatable in use, wherein the crushing surface has an axis extending in the general direction of a penis being circumcised in use and wherein the circumcision device includes a threaded nut which cooperates with the collar and with a threaded region of the glans penis locating and protecting member to operate the foreskin crushing assembly by axially moving the crushing surface relative to the crushing member closing a gap therebetween in use, and a cutting assembly rotatable about said axis relative to the crushing surface, the rotatable cutting assembly being located radially adjacent the crushing surface and held by the body so as to be capable of severing a foreskin crushed by the foreskin crushing assembly and wherein the rotatable cutting assembly includes a cutting blade movable between a first inoperative position in which it is radially withdrawn from the crushing surface and an operative position in which the blade extends towards the crushing surface for rotation about said axis to cooperate with the crushing surface or a foreskin located thereon so as, in use, to sever said foreskin.

2. The circumcision device as claimed in claim 1 wherein the cutting blade of the rotatable cutting assembly is carried by, or forms part of, a pivotally retractable blade arm that is attached to the rotatable cutting assembly at a mounted end of the blade arm by means of an articulated attachment so as to be movable between the first withdrawn inoperative position and the extended operative position in which the blade is located inwards of the articulated attachment and either trailing or leading the retractable blade arm.

3. The circumcision device as claimed in claim 2 wherein the blade has a second withdrawn inoperative position that may be reached by causing movement of the blade from an operative position past its first withdrawn inoperative position into said second withdrawn inoperative position in which it resists subsequent deployment to any operative position to thereby provide an optional expedient for rendering the circumcision device a single use circumcision device.

4. The circumcision device as claimed in claim 1 wherein the rotatable cutting assembly is configured such that a force applied to the rotatable cutting assembly urges the blade toward the crushing surface so as to cut any foreskin located on the crushing surface.

5. The circumcision device as claimed in claim 1 wherein the cutting assembly is configured such that a plurality of revolutions of the assembly are required to sever a foreskin located on the crushing surface.

6. The circumcision device as claimed in claim 1 wherein the crushing member is a crushing plate, and the rotatable cutting assembly includes two relatively rotatable components in the form of a base ring that is rotatable immediately adjacent the crushing plate carried by the body and a swivel ring that is rotatable to a limited extent relative to the base ring and that is held non-rotatable relative to the body by a removable tab or a frangible connection.

7. The circumcision device as claimed in claim 6 wherein one of the base ring and swivel ring has a pivot supporting a mounted end of the cutting blade carried by, or forming part of, a pivotally retractable blade arm.

8. The circumcision device as claimed in claim 7 wherein the other of the base ring and swivel ring has one or more formations for engaging the pivotally retractable blade arm to urge it inwards towards the crushing surface by transferring at least some of any rotational force applied to the rotatable cutting assembly.

9. The circumcision device as claimed in claim 7 wherein the swivel ring has a plurality of equally angularly spaced finger stops that are angularly spaced about the swivel ring and arranged to facilitate rotation in a direction corresponding to operative engagement of the cutting blade with a foreskin or crushing surface.

10. The circumcision device as claimed in claim 1 wherein the body is a separate component from the glans penis locating and protecting member and a series of differently sized glans penis locating and protecting members having like portions for common co-operation with the body and co-operating crushing plates is provided so that an appropriate size of glans penis locating and protecting member and co-operating crushing plate can be selected for use in conjunction with the body in respect of a particular patient.

11. The circumcision device as claimed in claim 1 wherein the crushing member is a crushing plate, wherein the crushing surface of the glans penis locating and protecting member is a divergent outer crushing surface thereof, and wherein the foreskin crushing assembly includes a peripheral crushing surface formed as or in a periphery of an aperture through the crushing plate attached to the body and with which the divergent outer crushing surface on the outside of the glans penis locating and protecting member co-operates.

12. The circumcision device as claimed in claim 11 wherein the crushing plate is fixed to the body and the collar is co-axial with, but spaced apart from, the aperture in the crushing plate with the collar being integral with the body.

13. The circumcision device as claimed in claim 12 wherein the glans penis locating and protecting member is tubular and has on the outside thereof projections co-operating with catches in a bore of the collar to prevent removal of the glans penis locating and protecting member from the body once a single use has been performed.

14. The circumcision device as claimed in claim 11 wherein the glans penis locating and protecting member has at least one formation for restricting its movement to axial movement without any rotation thereof.

* * * * *